US006931099B2

(12) United States Patent
Yamada et al.

(10) Patent No.: US 6,931,099 B2
(45) Date of Patent: Aug. 16, 2005

(54) HIGH-ENERGY X-RAY IMAGING DEVICE AND METHOD THEREFOR

(75) Inventors: Hironari Yamada, Shiga (JP); Isao Tooyama, Shiga (JP); Yasuji Kitazawa, Osaka (JP); Junichi Chikawa, Tokyo (JP)

(73) Assignee: Photon Production Laboratory Ltd., Hyogo-ken (JP)

( * ) Notice: Subject to any disclaimer, the term of this patent is extended or adjusted under 35 U.S.C. 154(b) by 116 days.

(21) Appl. No.: 10/398,911

(22) PCT Filed: Jan. 10, 2002

(86) PCT No.: PCT/JP02/00085

§ 371 (c)(1),
(2), (4) Date: Apr. 11, 2003

(87) PCT Pub. No.: WO02/061407

PCT Pub. Date: Aug. 8, 2002

(65) Prior Publication Data

US 2004/0013233 A1 Jan. 22, 2004

(30) Foreign Application Priority Data

Jan. 29, 2001 (JP) .......................................... 2001-19597

(51) Int. Cl.$^7$ ............................................... G21G 4/00
(52) U.S. Cl. .......................................... 378/119; 378/62
(58) Field of Search ............ 378/119, 62; 315/503–507

(56) References Cited

U.S. PATENT DOCUMENTS

| 4,365,341 A | * | 12/1982 | Lam ............................. 378/65 |
| 4,398,093 A | | 8/1983 | Dufay |
| 4,924,485 A | * | 5/1990 | Hoeberling ................. 378/102 |
| 5,033,095 A | | 7/1991 | Marcantonio |
| 6,201,851 B1 | * | 3/2001 | Piestrup et al. ............. 378/121 |
| 6,418,193 B1 | * | 7/2002 | Albagli ....................... 378/158 |

FOREIGN PATENT DOCUMENTS

| JP | 56-155900 A1 | | 12/1981 |
| JP | 3-503213 A1 | | 7/1991 |
| JP | 7-236632 A1 | | 9/1995 |
| JP | 07-236632 | * | 9/1995 |
| JP | 2000-46951 A1 | | 2/2000 |
| JP | 2001-27617 A1 | | 1/2001 |

* cited by examiner

Primary Examiner—Craig E. Church
Assistant Examiner—Jurie Yun
(74) Attorney, Agent, or Firm—Rader, Fishman & Grauer PLLC

(57) ABSTRACT

The present invention relates to a high-energy X-ray imaging device that is suitable for precise medical diagnosis and capable of enhancing the accuracy of nondestructive examinations. The high-energy X-ray imaging device of the present invention includes an electron-circulating type high luminance X-ray generator and a two-dimensional X-ray detector that is sensitized for high-energy X-rays. The electron-circulating type X-ray generating device consists of a tinytarget together with a LINAC or microtron injector and a synchrotron. The synchrotron stores electrons, and electrons are bombarded against a tinytarget placed on the electron orbit to generate high-energy X-rays. The means to sensitize the two-dimensional X-ray detectors consists of a thin film made of lead or other heavy elements. This thin film is placed in front of and in close contact with the two-dimensional detector, such as X-ray film. The X-ray image thus generated is a transmissive image.

5 Claims, 3 Drawing Sheets

HIGH-ENERGY X-RAY IMAGING DEVICE AND METHOD THEREFOR

TECHNICAL FIELD

The present invention relates to a high-energy X-ray imaging device to be employed in industrial applications that use X-rays. Specifically, the present invention relates to a high-energy X-ray imaging device that is most suitable for radiography, X-ray therapy, nondestructive examinations, radioscopy, two-dimensional fluorescent X-ray analysis, topography, X-ray microscopy, and other X-ray related technologies.

BACKGROUND ART

Radiography uses approximately 60 keV X-rays. It has served humanity for the past 100 years, and has been increasingly popular in recent years. The upper limit for X-rays used in nondestructive examinations is approximately 150 keV. Absorption contrast is used to image objects in radiography and nondestructive examinations. High-energy X-rays have not been used in the past, except in nondestructive examination of structures, because of their high transmissivity. The spatial resolution of absorption images is limited due to the scattering of X-rays.

Medical exposure is one of the problems in radiography. X-rays of about 60 keV are significantly absorbed into the body so that several rounds of exposure can easily exceed the legal limit. Both doctors and patients are exposed to serious danger when an operation must be carried out under X-ray visualization. Another problem is the accuracy of X-ray images. It is difficult to identify a cancerous region of 1 mm or less. In a nondestructive examination, it is difficult to get sharp images due to the scattering of X-rays. The absorption method, when high-energy X-rays or gamma rays are used, is not suitable for imaging light elements, that is, living organisms and animate matter.

The objective of the present invention is to provide a high-energy X-ray imaging device that generates high luminance and high-energy X-rays using an electron-circulating type X-ray generating device.

It uses high-energy X-rays of 100 keV to several tens of MeV that have never been used before, and the device images transmittable X-ray images of high accuracy aided by a two-dimensional X-ray detector in which its detection sensitivity is increased by the use of a thin film made of lead or other heavy elements. The high-energy X-ray imaging device also produces very fine images of both structures and bio-substances made up of light elements using the effect of refraction interference arising from the phase shift of X-rays due to density.

DISCLOSURE OF INVENTION

The technical resolution means adopted by the present invention is: A high-energy X-ray imaging device comprising an X-ray generating device that uses relativistic electrons and a two-dimensional X-ray detector, wherein said X-ray generating device generates high-energy X-rays, and said two-dimensional X-ray detector detects high-energy X-rays that pass through the body being tested.

Said high-energy X-ray imaging device may include, as said X-ray generating device, tinytarget together with a LINAC, microtron, betatron, or electron-circulating type X-ray generating device using synchrotron, or electron-storage ring.

Said high-energy X-ray imaging device may include said X-ray generating device in which the electron energy is controlled at 8 MeV or below.

Said high-energy X-ray imaging device may use, as said two-dimensional X-ray detector, at least one X-ray film, nuclear dry plate, imaging plate, X-ray tube or CCD camera for imaging.

Said high-energy X-ray imaging device may be provided, upstream of said two-dimensional X-ray detector, a thin plate made of lead, tungsten, gold, platinum, silver, tin, antimony or other heavy elements for the purpose of enhancing the efficiency of high-energy X-ray detection.

To enhance the efficiency of detection by said two-dimensional X-ray detector, said high-energy X-ray imaging device may be provided, downstream of said thin plate, a fluorescent plate in close contact with said two-dimensional X-ray detector, or fluorescent substances may be coated or deposited on the thin plate on the surface facing said two-dimensional detector, or the fluorescent substances may be coated or deposited on the detecting surface of said two-dimensional X-ray detector.

Said high-energy X-ray imaging device may also include, upstream of the body being tested, a low-energy X-ray absorbent for the purpose of reducing low-energy X-ray exposure and enhancing the resolution of X-ray images.

Said high-energy X-ray imaging device may use, as the low-energy X-ray absorbent, a plate made of beryllium, polymer membrane, graphite, aluminum, silicon, iron, copper, nickel or other light elements.

It is another objective of the present invention to provide a high-energy X-ray imaging method wherein high-energy X-rays, generated by an X-ray generating device using relativistic electrons, are irradiated onto the target and the transmissive X-rays are imaged as two-dimensional images.

BEST MODE FOR CARRYING OUT THE INVENTION

Figure 1:
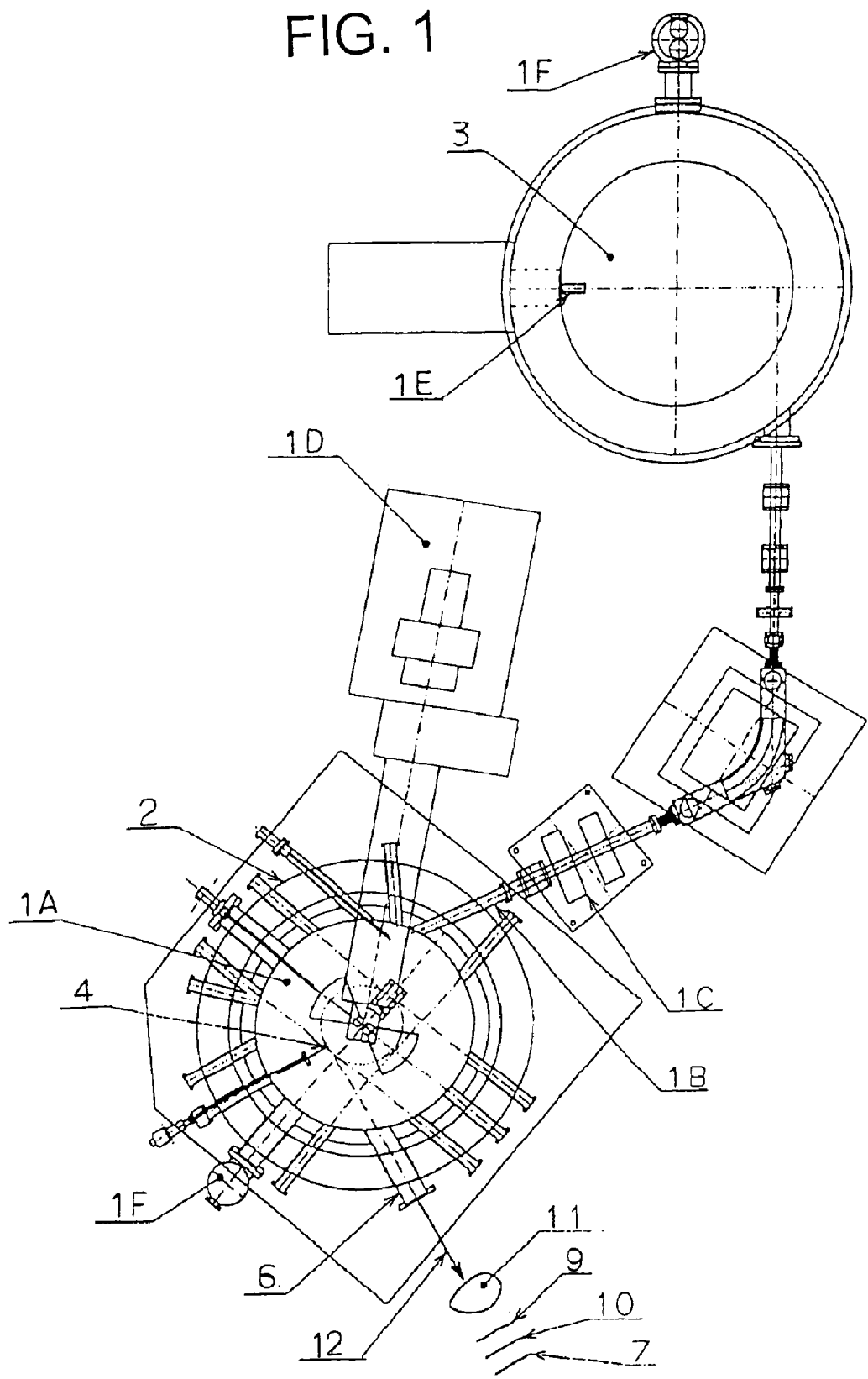
FIG. 1 is a general plan view illustrating the high-energy X-ray imaging device of the present invention.

The high-energy X-ray imaging device of the present invention is described in detail using FIG. 1. FIG. 1 is a general plan view of the device. The high-energy X-ray imaging device of the present invention incorporates the electron-circulating type X-ray generating device 1 as a means of generating X-rays using relativistic electrons. X-ray luminance of the electron-circulating type X-ray generating device, which has a very small source point thus the device is suitable for the high-energy X-ray imaging device of the present invention. It is possible to generate X-rays by irradiating relativistic electrons generated by a LINAC, microtron, betatron or synchrotron onto the tinytarget or by placing the tinytarget on the orbit of the relativistic electrons generated by the LINAC, microtron, betatron or synchrotron. The electron-circulating type X-ray generating device shown in FIG. 1 is a known type. It consists of a vacuum tank 1A, electron-storing ring 2, incident port 1B guiding electrons into the vacuum tank 1A, Q magnet 1C, klystron 1D, electron gun 1E, vacuum pump 1F, beam line 1G, and microtron injector 3. High luminance X-rays are generated by placing a target on the electron orbit of the electron-storing ring 2 and by storing electrons. In this FIG. 1, the electron beam injector is a small microtron 3. The electron energy of the microtron is 6 MeV. This level of energy is adopted because nuclear reaction does not occur when the electron energy is below 8 MeV. Accordingly, the device of the present invention does not generate neutrons thus lead and iron are used to shield radiation; concrete shields are not necessary. Electrons of 6 MeV enter and are stored on the electron-storing ring 2 and a tiny solid target 4 is placed on the electron orbit to generate X-rays. The target is a thin wire of tungsten, gold, lead, etc. several microns to several millimeters in diameter, and a thin film may also be used as well as Si and other crystals.

X-ray beam 12 is extracted through the beam line 6 shown in FIG. 1. The spread of the X-ray beam 12 is approximately 0.08 rad. Accordingly, the size of the window of the beam line 6 is approximately 10 cm in diameter. The vacuum window of the beam line 6 is made of approximately 1 mm thick aluminum to absorb low-energy X-rays. That is, the beam line 6 has another function that is reducing low-energy X-ray exposure. It is recommended that the thickness be varied according to the application. This particular X-ray generating device emits soft X-rays also. To facilitate replacement of low-energy absorbents, a polymer thin film of beryllium, plastics, etc., or approximately 0.1 mm thick aluminum is used as the window material, and X-ray absorbents are placed separately. The X-ray absorbent is optimized by varying the thickness of the beryllium, polymer film or aluminum. Various thin films can be used such as gold, lead or tin. However, use of lead, gold and other heavy elements will generate fluorescent X-rays, and these become a new source of X-ray emissions resulting in increased imaging defects. Use of heavy metals is therefore not recommended.

The two-dimensional X-ray detector 7 shown in FIG. 1 is described below.

The two-dimensional X-ray detector 7 detects X-rays that pass through the body being tested. It has the same structure as an X-ray detector of a known X-ray inspection system. The detector is placed facing the above-mentioned-beam line 6. As the detector 7, an X-ray film, nuclear dry plate, CCD camera for X-rays, X-ray tube, imaging plate or other commercially available part is used. In FIG. 1, an X-ray film is used as the X-ray detector 7. To enhance the efficiency of X-ray detection in the present invention, a (thin) lead plate 9, several microns to several mm thick, is placed in front of and in close contact with these X-ray detectors 7. The thin lead plate 9 is used to vary the wavelength of the X-rays. A 0.1 mm thick lead plate 9 is used in this particular example. The X-ray spectrum of the electron-circulating type X-ray generating device ranges from several keV to 6 MeV. High-energy X-rays of 80 keV and above are absorbed due to the photoelectric effect of the lead and emitted again as low-energy fluorescent X-rays, which are detected by the X-ray film 7. Within the lead material, the high-energy X-rays generate electrons by Compton scattering. X-ray film 7 is highly sensitive to these electrons and the electrons thus generated also generate bremsstrahlung, further increasing the low-energy X-rays.

Furthermore, electron pairs are generated when X-rays of 1.1 MeV and above enter the lead material. The X-ray film 7 is also highly sensitive to the electrons and positrons generated in this way. The wavelength varying materials are not limited to lead. Since heavy elements have a high conversion efficiency, tungsten, gold, platinum, silver, tin and antimony are all good materials for the thin plate 9, though the conversion efficiency is lower than that of lead.

Another advantage of placing a thin lead film 9 in front of the X-ray film 7 is to cut off X-rays of 80 kV and below. X-ray linearity is proportional to the energy level. Low-energy X-rays are easily scattered. The scattered X-rays at the specimen or the body being tested 11 and beam line 6 are the cause of blurred X-ray images. Thin lead plates are an effective means of eliminating this cause.

The use of fluorescent plate 10 is described below. This plate may or may not be used. Fluorescent plates have a sensitizing effect, that is, a fluorescent plate converts X-rays to visible light, thereby enhancing the film's sensitivity. The problem is that the derived image is blurred depending on the thickness of the fluorescent plate. To avoid this problem, fluorescent substances are directly coated or deposited on the thin lead plate 9 on the surface facing the two-dimensional X-ray detector 7. It is also possible to coat the fluorescent substances directly on the surface of the detector 7. It is also good to use nuclear dry plates as high-energy X-ray film.

Figure 2:
FIG. 2 is a photograph of a swallowtail butterfly photographed by the high-energy X-ray imaging device.

X-ray photographs derived from the high-energy X-ray imaging device of the present invention are shown in the attached figures. The solid target 4 is a 0.5 mm tungsten wire. The vacuum window is made of 1 mm thick aluminum. The sensitizing material used is a 0.2 mm thin lead film. The X-ray film used is an ordinary direct radiographic film. The specimen and the film are in direct contact with each other in these examples. Even when they are separated by 1 meter, an image of the same contrast can be obtained except that the size is approximately doubled. FIG. 2 is an image of a swallowtail butterfly. No fluorescent plate was used for this image. The image clearly shows the structure constructed by light elements such as the body, skeleton, interior of the eyes, tactile organ, straw, gussets on the abdomen and the profiles of particulate matter. It is not definitely known why a butterfly made of light elements can be so sharply imaged with high-energy X-rays, but this is probably because of interference of the X-rays. X-rays will shift phase according to the difference of density and they are refracted. At the boundaries where different densities meet, refracted X-rays interfere with non-refracted X-rays and generate light-and-dark interference patterns. Phase shifting of X-rays greatly depends on the density of the substances photographed. Interference occurs at the boundaries of substances of different densities and depict the boundary sharply. For example, cancer cells and healthy cells have a similar element structure but have different densities. This is the reason why the high-energy X-ray imaging device of the present invention can easily identify cancer cells.

Figures 3A, 3B:
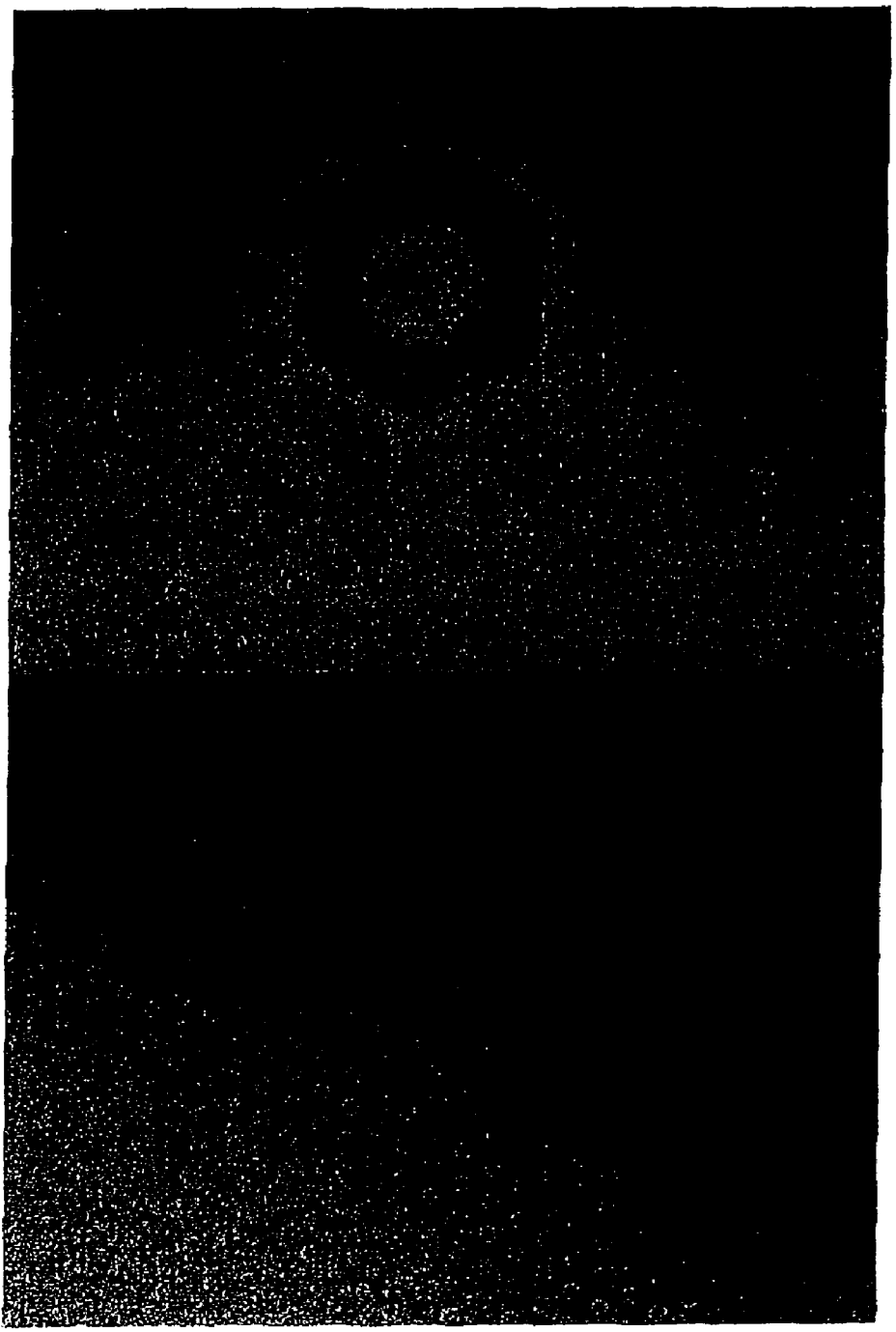
FIG. 3A is a stainless steel nut.
FIG. 3B is a 1 mm thick aluminum mesh, both photographed by the high-energy X-ray imaging device of the present invention.

FIG. 3A is a steel nut. This and the next sample were imaged using a fluorescent plate. The 4 mm thick stainless steel nut was imaged by transmission just as though we were looking at a pane of glass. Only high-energy X-rays produce X-ray images like this. The top and bottom surfaces of the nut are also clearly imaged. FIG. 3 is a 1 mm mesh made of 1 mm thick aluminum. This is also a transmission image. Light-and-dark contrast occurs around the openings of the mesh, showing that this is also an interference image.

The above description shows that the high-energy X-ray imaging device of the present invention provides transmission X-ray images of very high precision, and is suitable for imaging both light and heavy elements. The device exhibits excellent performance in both medical diagnosis and non-destructive examinations. Furthermore, since high-energy X-rays have high transmissivity and are hardly absorbed in the human body, the device of the present invention significantly reduces exposure to radiation.

The present invention may be implemented in any other form of embodiment without deviating from the spirit of the main features thereof. The above-mentioned embodiments are therefore only a few examples and should not be construed as limiting.

INDUSTRIAL APPLICABILITY

As detailed above, the high-energy X-ray imaging device of the present invention generates high luminance high-energy X-rays using its electron-circulating type X-ray generating device. It uses high-energy X-rays of 100 keV to several tens of MeV that have not been used in conventional devices. The detection sensitivity of the two-dimensional X-ray detector is enhanced by using thin films made of lead and other heavy elements to aid in the generation of transmissive high-precision X-ray images. The high-energy X-ray imaging device of the present invention uses the phenomenon in which the phase of the X-rays is shifted by density and triggers refraction interference, and therefore is sensitive to the boundaries of substances. For this reason the high-energy X-ray imaging device of the present invention generates precise images for not only bio-substances made of light elements but also structures. For example, the device identifies cancer cells and healthy cells because they have different densities. It is also possible to identify types of cancers by noting differences in shape. High-energy X-rays have high transmissivity, and as a result, the device offers the remarkable effect of reducing exposure to radiation in medical applications.

What is claimed is:

1. A high-energy X-ray imaging device comprising:
   an X-ray generating device that uses relativistic electrons, said X-ray generating device including a target and one of a synchrotron and an electron storing ring;
   a two-dimensional X-ray detector; and
   a thin plate located upstream of said two-dimensional detector, wherein said thin plate is made of lead, tungsten, gold, platinum, silver, tin, antimony or other heavy elements in order to enhance the efficiency of high-energy X-ray detection,
   wherein said X-ray generating device generates high-energy X-rays and said two-dimensional X-ray detector detects high-energy X-rays that pass through a body being tested,
   wherein said target is located on an electron orbit of the one of said synchrotron and electron-storing ring, and
   wherein one of an X-ray film, nuclear dry plate, imaging plate, X-ray tube and CCD camera for imaging is used as said two-dimensional X-ray detector.

2. A high-energy X-ray imaging device comprising:
   an X-ray generating device that uses relativistic electrons, said X-ray generating device including a target and one of a synchrotron and an electron storing ring; and
   a two-dimensional X-ray detector; and
   a thin plate located upstream of said two-dimensional detector, wherein said thin plate is made of lead tungsten, gold, platinum, silver, tin, antimony or other heavy elements in order to enhance the efficiency of high-energy X-ray detection; and
   a fluorescent plate located downstream of said two-dimensional X-ray detector, is in close contact with said two-dimensional X-ray detector, and is a plate in addition to said thin plate, or fluorescent substances are coated or deposited on said thin plate on a surface facing said two-dimensional detector, or the fluorescent substances are coated or deposited on a detecting surface of said two-dimensional X-ray detector to enhance efficiency of X-ray detection by said two-dimensional X-ray detector,
   wherein said X-ray generating device generates high-energy X-rays and said two-dimensional X-ray detector detects high-energy X-rays that pass through a body being tested,
   wherein said target is located on an electron orbit of the one of said synchrotron and electron-storing ring, and
   wherein one of an X-ray film, nuclear dry plate, imaging plate, X-ray tube and CCD camera for imaging is used as said two-dimensional X-ray detector.

3. A high energy X-ray imaging method comprising the steps of:
   generating high-energy X-rays that uses relativistic electrons, a target, and one of a synchrotron and an election storage ring;
   detecting the high-energy X-rays at a two-dimensional X-ray detector;
   directing the high-energy X-rays through a thin plate, wherein the thin plate is located upstream of the two-dimensional X-ray detector; and
   transmitting the high-energy X-rays through a fluorescent plate located downstream from the thin plate,
   wherein the high-energy X-rays generated are irradiated onto an object and the transmitted X-rays are captured to generate two-dimensional images.

4. A high energy X-ray generating device comprising:
   an X-ray generating device that uses relativistic electrons, said X-ray generating device including a target and one of a synchrotron and an electron storing ring;
   a two-dimensional X-ray detector;
   a thin plate located upstream of said two-dimensional X-ray detector; and
   a fluorescent plate is located downstream of said thin plate,
   wherein said X-ray generating device generates high-energy X-rays and said two-dimensional X-ray detector detects high-energy X-rays that pass through a body being tested, and
   wherein said target is located on an electron orbit of the one of said synchrotron and electron-storing ring.

5. A high-energy X-ray imaging device comprising:
   an X-ray generating device that uses relativistic electrons, said X-ray generating device including a target and one of a synchrotron and an electron storing ring;
   a two-dimensional X-ray detector;
   a thin plate located upstream of said two-dimensional X-ray detector; and
   a fluorescent plate is located downstream of said thin plate,
   wherein said X-ray generating device generates high-energy X-rays and said two-dimensional X-ray detector detects high-energy X-rays that pass through a body being tested, and
   wherein said target is located on an electron orbit of the one of said synchrotron and electron-storing ring.

* * * * *